United States Patent [19]

Bharadwaj et al.

[11] Patent Number: 6,166,283
[45] Date of Patent: Dec. 26, 2000

[54] ON-LINE SYNTHESIS AND REGENERATING OF A CATALYST USED IN AUTOTHERMAL OXIDATION

[75] Inventors: Sameer S. Bharadwaj; Joseph J. Maj; Jonathan H. Siddall, all of Midland, Mich.

[73] Assignee: The Dow Chemical Company, Midland, Mich.

[21] Appl. No.: 09/388,220

[22] Filed: Sep. 1, 1999

Related U.S. Application Data

[63] Continuation of application No. 60/099,041, Sep. 3, 1998, which is a continuation of application No. 60/111,861, Dec. 11, 1998, and a continuation of application No. 60/136,003, May 26, 1999.

[51] Int. Cl.[7] .......................... C07C 5/327; C07C 5/373; C07C 5/333
[52] U.S. Cl. .......................... 585/658; 585/660; 585/656; 585/661
[58] Field of Search .................................. 585/658, 660, 585/656, 661

[56] References Cited

U.S. PATENT DOCUMENTS

| | | | |
|---|---|---|---|
| 3,670,044 | 6/1972 | Drehman et al. | 260/683.3 |
| 4,902,849 | 2/1990 | McKay et al. | 585/660 |
| 4,940,826 | 7/1990 | Font Freide et al. | 585/600 |
| 5,073,657 | 12/1991 | Warren | 585/500 |
| 5,105,052 | 4/1992 | Font Freide et al. | 585/651 |
| 5,382,741 | 1/1995 | Astbury et al. | 585/652 |
| 5,625,111 | 4/1997 | Astbury et al. | 585/653 |
| 5,639,929 | 6/1997 | Bharadwaj et al. | 585/658 |
| 5,648,582 | 7/1997 | Schmidt et al. | 585/652 |
| 5,654,491 | 8/1997 | Goetsch et al. | 568/469.9 |
| 5,905,180 | 5/1999 | Yokoyama et al. | 585/658 |

FOREIGN PATENT DOCUMENTS

| | | |
|---|---|---|
| 0 412 415 A1 | 2/1991 | European Pat. Off. . |
| 42 00 006 A1 | 7/1993 | Germany . |

OTHER PUBLICATIONS

C. Yokoyama, S.S. Bharadqaj, and L.D. Schmidt, "Platinum–Tin and Platinum–Copper Catalysts for Autothermal Oxidative Dehydration of Ethane to Ethylene," Catalysis Letters, 38 (1996), 181–188.

*Primary Examiner*—Marian C. Knode
*Assistant Examiner*—Thuan D. Dang

[57] ABSTRACT

An on-line method of synthesizing or regenerating catalysts for autothermal oxidation processes, specifically, the oxidation of paraffinic hydrocarbons, for example, ethane, propane, and naphtha, to olefins, for example, ethylene and propylene. The catalyst comprises a Group 8B metal, for example, a platinum group metal and, optionally, a promoter, such as tin, antimony, or copper, on a support, preferably a monolith support. On-line synthesis or regeneration involves co-feeding a volatile Group 8B metal compound and/or a volatile promoter compound with the paraffinic hydrocarbon and oxygen into the oxidation reactor under ignition or autothermal conditions.

22 Claims, No Drawings

ON-LINE SYNTHESIS AND REGENERATING OF A CATALYST USED IN AUTOTHERMAL OXIDATION

CROSS-REFERENCES TO RELATED APPLICATIONS

This application claims the benefit of U.S. Provisional Application Ser. No. 60/099,041, filed Sep. 3, 1998, U.S. Provisional Application Ser. No. 60/111,861, filed Dec. 11, 1998, and U.S. Provisional Application Ser. No. 60/136,003, filed May 26, 1999.

BACKGROUND OF THE INVENTION

The present invention relates to catalytic autothermal oxidation processes. More particularly, the present invention relates to a method of regenerating a catalyst used in the catalytic partial oxidation of paraffinic hydrocarbons, such as ethane, propane, and naphtha, to olefins, such as ethylene and propylene.

Olefins find widespread utility in industrial organic chemistry. Ethylene is needed for the preparation of important polymers, such as polyethylene, vinyl plastics, and ethylene-propylene rubbers, and important basic chemicals, such as ethylene oxide, styrene, acetaldehyde, ethyl acetate, and dichloro-ethane. Propylene is needed for the preparation of polypropylene plastics, ethylene-propylene rubbers, and important basic chemicals, such as propylene oxide, cumene, and acrolein. Isobutylene is needed for the preparation of methyl tertiary butyl ether. Long chain mono-olefins find utility in the manufacture of linear alkylated benzene sulfonates, which are used in the detergent industry.

Low molecular weight olefins, such as ethylene, propylene, and butylene, are produced almost exclusively by thermal cracking (pyrolysis/steam cracking) of alkanes at elevated temperatures. An ethylene plant, for example, typically achieves an ethylene selectivity of about 85 percent calculated on a carbon atom basis at an ethane conversion of about 60 mole percent. Undesired coproducts are recycled to the shell side of the cracking furnace to be burned, so as to produce the heat necessary for the process. Disadvantageously, thermal cracking processes for olefin production are highly endothermic. Accordingly, these processes require the construction and maintenance of large, capital intensive, and complex cracking furnaces. The heat required to operate these furnaces at a temperature of about 900° C. is frequently obtained from the combustion of methane which disadvantageously produces undesirable quantities of carbon dioxide. As a further disadvantage, the crackers must be shut down periodically to remove coke deposits on the inside of the cracking coils.

Catalytic processes are known wherein paraffinic hydrocarbons are oxidatively dehydrogenated to form mono-olefins. In these processes, a paraffinic hydrocarbon is contacted with oxygen in the presence of a catalyst consisting of a platinum group metal or mixture thereof deposited on a ceramic monolith support, typically in the form of a honeycomb or foam. Optionally, hydrogen may be a component of the feed. The catalyst, prepared using conventional techniques, is uniformly loaded throughout the support. The process can be conducted under autothermal reaction conditions wherein the feed is partially combusted, and the heat produced during combustion drives the endothermic cracking processes. Consequently, under autothermal process conditions there is no external heat source required; however, the catalyst is required to support combustion above the normal fuel-rich limit of flammability. Representative references disclosing this type of process include the following U.S. Pat. Nos.: 4,940,826; 5,105,052; 5,382,741; and 5,625,111. Disadvantageously, substantial amounts of deep oxidation products, such as carbon monoxide and carbon dioxide, are produced, and the selectivity to olefins remains too low when compared with thermal cracking. Moreover, the references are silent with respect to a method of regenerating the catalyst.

M. Huff and L. D. Schmidt disclose in the *Journal of Physical Chemistry*, 97, 1993, 11,815, the production of ethylene from ethane in the presence of air or oxygen under autothermal conditions over alumina foam monoliths coated with platinum, rhodium, or palladium. A similar article by M. Huff and L. D. Schmidt in the *Journal of Catalysis*, 149, 1994, 127–141, discloses the autothermal production of olefins from propane and butane by oxidative dehydrogenation and cracking in air or oxygen over platinum and rhodium coated alumina foam monoliths. Again, the olefin activity achieved in these processes could be improved. The references are also silent with respect to a method of regenerating the catalyst.

U.S. Pat. No. 5,639,929 teaches an autothermal process for the oxidative dehydrogenation of $C_2$–$C_6$ alkanes with an oxygen-containing gas in a fluidized catalyst bed of platinum, rhodium, nickel, or platinum-gold supported on alpha alumina or zirconia. Ethane produces ethylene, while higher olefins produce ethylene, propylene, and isobutylene. Again, the olefin selectivity could be improved, and the reference is silent with respect to a method of regenerating the catalyst.

C. Yokoyama, S. S. Bharadwaj and L. D. Schmidt disclose in *Catalysis Letters*, 38, 1996, 181–188, the oxidative dehydrogenation of ethane to ethylene under autothermal reaction conditions in the presence of a bimetallic catalyst comprising platinum and a second metal selected from tin, copper, silver, magnesium, cerium, lanthanum, nickel, cobalt, and gold supported on a ceramic foam monolith. The use of a catalyst comprising platinum with tin and/or copper results in an improved olefin selectivity; however, over time at high operating temperatures the second metal vaporizes off the catalyst and catalytic activity decreases. When this occurs the reactor must be shut down to replace or regenerate the catalyst.

In view of the above, it would be desirable to discover an autothermal catalytic process of oxidizing a paraffinic hydrocarbon to an olefin wherein the catalyst can be readily regenerated. Such a process would provide the benefits of catalytic autothermal processes, such as low levels of catalyst coking and simplified engineering, with the added benefit of easy catalyst regenerability. It would be even more desirable if a catalytic autothermal process providing easy catalyst regenerability was to achieve a paraffinic hydrocarbon conversion and an olefin selectivity comparable to those achieved by commercial thermal cracking processes.

SUMMARY OF THE INVENTION

This invention is a process of synthesizing or regenerating a catalyst used in an autothermal catalytic oxidation process. In a preferred embodiment, the oxidation process involves contacting a paraffinic hydrocarbon or a mixture of paraffinic hydrocarbons with oxygen in an oxidation reactor in the presence of the catalyst under autothermal process conditions sufficient to form at least one olefin. Hereinafter, the feed comprising the paraffinic hydrocarbon and oxygen, and optionally hydrogen, may be referred to simply as the "reactant feedstream" or, more simply, the "feedstream."

The catalyst used in this oxidation process comprises at least one Group 8B metal and, optionally, at least one promoter supported on a catalyst support, preferably a monolith support.

The catalyst synthesis/regeneration process of this invention is conducted "on-line," which means that the support, either blank or in the form of a deactivated or partially deactivated catalyst, is loaded in the reactor and maintained under ignition or autothermal process conditions. The "blank" support is a fresh support absent any Group 8B metal and promoters.

The process of this invention, which involves synthesizing or regenerating a catalyst which is used in the autothermal oxidation of paraffinic hydrocarbons to olefins, comprises feeding a volatile Group 8B metal compound and/or a volatile promoter compound into the oxidation reactor simultaneously with the reactant feedstream under ignition conditions or autothermal process conditions. Mixtures of volatile Group 8B metal compounds and/or volatile promoter compounds can also be employed. In the reactor the volatile Group 8B metal compound and the volatile promoter compound contact the front face of the support where they decompose at the high temperature of the ignition or autothermal conditions into the corresponding Group 8B metal and/or promoter components.

The aforementioned method of this invention beneficially allows for the synthesis of an oxidation catalyst on-line or alternatively, allows for the regeneration of a deactivated or partially deactivated oxidation catalyst on-line. The method of this invention eliminates the necessity of preparing the catalyst prior to loading the reactor and eliminates the necessity of shutting down the reactor to regenerate or replace the deactivated catalyst. Additionally, novel catalyst compositions can be prepared and screened on-line for catalytic activity. The regeneration can be beneficially employed on-line to replace metal components of the catalyst which are lost over time through vaporization. Dead sections of the catalyst can be reactivated on-line. As a further advantage, the method of this invention is readily engineered by simply introducing the volatile compounds into the reactant feedstream. There is no necessity, for example, to construct complicated spray devices or separate ports within the reactor.

Another advantage relates to reactor design. In one preferred embodiment, the reactor for this process comprises a housing, such as a tube, into which the catalyst, in the form of catalytic components deposited onto a monolith support, is packed. One or more radiation shields are typically packed on either side of the catalyst to reduce radiation heat losses. The radiation shield typically consists of a bare monolith support absent any catalytic metals. The entire reactor is insulated to maintain essentially adiabatic conditions. The reactant feedstream flows through an entrance port into the reactor, passes through the front radiation shield, and then contacts the catalyst. The effluent stream passes through the downstream radiation shield and exits the reactor. Advantageously, in the synthesis/regeneration process of this invention there is no necessity to remove the front radiation shield from the reactor, because the volatile Group 8B metal compound and the volatile promoter compound used in the synthesis/regeneration process pass through the front radiation shield with the reactant feedstream on the path to the catalyst. Moreover, uniform deposition of the volatile Group 8B metal compound and volatile promoter compound onto the front edge of the catalyst may be achieved with minimum, if any, deposition onto extraneous surfaces.

All of the aforementioned advantages simplify the handling and maintenance of the catalyst, reduce costs, and improve process efficiency.

In another aspect, this invention is an improved process of oxidizing a paraffinic hydrocarbon or mixture of paraffinic hydrocarbons to an olefin or a mixture of olefins. The process involves contacting a paraffinic hydrocarbon or mixture of paraffinic hydrocarbons and oxygen in an oxidation reactor in the presence of a catalyst under autothermal process conditions, and either continuously or intermittently feeding a volatile Group 8B metal compound and/or a volatile promoter compound, or a mixture thereof, into the reactor with the feedstream. The catalyst, as noted hereinbefore, comprises at least one Group 8B metal and, optionally, at least one promoter supported on a catalyst support, preferably a monolith support.

The autothermal oxidation process of this invention efficiently produces olefins, particularly mono-olefins, from paraffinic hydrocarbons and oxygen. Advantageously, the process of this invention achieves a paraffin conversion and olefin selectivity which are comparable to commercial thermal cracking processes. As a further advantage, the process produces little, if any, coke, thereby substantially prolonging catalyst lifetime and eliminating the necessity to shut down the reactor to remove coke deposits. The process of this invention employs a simple engineering design thereby eliminating the requirement for a large, expensive, and complex furnace, such as those used in thermal cracking processes. More specifically, since the residence time of the reactants in the process of this invention is on the order of milliseconds, the reaction zone used in this process operates at high volumetric throughput. Accordingly, the reaction zone measures from about one-fiftieth to about one-hundredth the size of a commercially available steam cracker of comparable capacity. The reduced size of the reactor lowers costs and greatly simplifies catalyst loading and maintenance procedures. As a further advantage, since the process of this invention is exothermic, the heat produced can be harvested via integrated heat exchangers to produce electrical energy or steam credits for other processes. Finally, the improved autothermal oxidation process of this invention characterized by on-line regeneration of the catalyst achieves long run times without interruption.

DETAILED DESCRIPTION OF THE INVENTION

The processes of this invention, described hereinafter, relate to the autothermal partial oxidation of paraffinic hydrocarbons to olefins. The words "partial oxidation" imply that the paraffinic hydrocarbon is not substantially oxidized to deep oxidation products, specifically, carbon monoxide and carbon dioxide. Rather, the partial oxidation comprises one or both of oxidative dehydrogenation and cracking to form primarily olefins. It is not known or suggested to what extent or degree either process, oxidative dehydrogenation or cracking, predominates or occurs to the exclusion of the other.

The oxidation process comprises contacting a paraffinic hydrocarbon or mixture of paraffinic hydrocarbons with oxygen in the presence of a catalyst under autothermal process conditions sufficient to form one or more olefins. Optionally, the process can be conducted in the presence of hydrogen, preferably, co-fed with the paraffinic hydrocarbon and oxygen. Together the paraffinic hydrocarbon and oxygen, and optionally hydrogen, comprise the reactant feedstream. The catalyst employed in the process comprises at least one Group 8B metal and, optionally, at least one promoter supported on a catalyst support, preferably a monolith support.

In one aspect, the process of this invention comprises a method of synthesizing or regenerating the aforementioned oxidation catalyst. The method comprises co-feeding a volatile Group 8B metal compound and/or a volatile promoter compound into the oxidation reactor simultaneously with the reactant feedstream under ignition or autothermal process conditions.

More specifically, the process of this invention comprises a method of synthesizing the aforementioned oxidation catalyst. The method comprises co-feeding a volatile Group 8B metal compound and, optionally, a volatile promoter compound into the oxidation reactor simultaneously with the reactant feedstream. In the reactor the volatile Group 8B metal compound and, optionally, the volatile promoter compound, contact a blank catalyst support and at the high ignition temperature decompose into the corresponding Group 8B metal and promoter, thereby forming the oxidation catalyst.

In another aspect, the process of this invention comprises regenerating the aforementioned oxidation catalyst after it has become deactivated or partially deactivated. The process comprises co-feeding a volatile Group 8B metal compound and/or a volatile promoter compound into the oxidation reactor simultaneously with the reactant feedstream. If the catalyst is partially deactivated, then autothermal process conditions can be employed. If the catalyst is fully deactivated, then ignition conditions can be employed. The volatile compounds contact the deactivated or partially deactivated catalyst and at the high temperature employed decompose into the corresponding Group 8B metal and/or promoter, thereby regenerating the catalyst.

In the synthesis/regeneration process described hereinabove, it is also acceptable to employ more than one volatile Group 8B metal compound and/or more than one volatile promoter compound. Moreover, in the process described hereinabove, the words "volatile Group 8B metal compound" and "volatile promoter compound" are meant to include volatile compounds in which the Group 8B metal or promoter are bonded to other elements in a molecular composition. Additionally, the language is meant to include a vapor stream of the Group 8B metal and/or promoter in their elemental form. Normally, one skilled in the art might not regard a vapor stream of an element as a volatile "compound;" however, for the purposes of this invention the term "volatile compound" will include the elemental vapor.

In another aspect, this invention is an improved autothermal process of oxidizing paraffinic hydrocarbons to olefins. In this aspect, the invention comprises contacting a paraffinic hydrocarbon or mixture thereof with oxygen in the presence of the aforementioned oxidation catalyst under autothermal process conditions, and simultaneously, feeding into the reactant feedstream a volatile Group 8B metal compound and/or a volatile promoter compound, or a mixture thereof, under autothermal process conditions.

In a preferred embodiment of this invention, the paraffinic hydrocarbon is selected from ethane, propane, mixtures of ethane and propane, naphtha, gas oils, vacuum gas oils, natural gas condensates, and mixtures of the aforementioned hydrocarbons; and the preferred olefins are ethylene, propylene, butene, isobutylene, and butadiene.

In another preferred embodiment, the Group 8B metal is a platinum group metal; more preferably, the platinum group metal is platinum.

Typically, the promoter is selected from the elements and ions of Groups 1B (Cu, Ag, Au), 6B (Cr, Mo, W), 3A (for example, Al, Ga, In), 4A (for example, Ge, Sn, Pb), and 5A (for example, As, Sb, Bi) of the Periodic Table of the Elements, as referenced by S. R. Radel and M. H. Navidi, in Chemistry, West Publishing Company, New York, 1990. In a broader context, however, the promoter can include support modifiers, which are defined as any ion having a charge of +1 or greater selected from Groups 1A (Li, Na, K, Rb, Cs), 2A (for example, Mg, Ca, Sr, Ba), 3B (Sc, Y, La), 4B (Ti, Zr, Hf), 5B (V, Nb, Ta), 6B (Cr, Mo, W), 1B (Cu, Ag, Au), 3A (for example, Al, Ga, In), 4A (for example, Ge, Sn, Pb), 5A (for example, As, Sb, Bi), and the lanthanide rare earths (for example, Ce, Er, Lu, Ho) and actinide elements (for example, Th) of the Periodic Table, previously referenced to S. R. Radel and M. H. Navidi, ibid. (Groups 1A, 2A, 3B, 4B, 5B, 6B, 1B, 3A, 4A, and 5A of the Periodic Table are equivalent to Groups 1, 2, 3, 4, 5, 6, 11, 13, 14, and 15.) The preferred promoter is selected from the elements and ions of Groups 1B, 6B, 3A, 4A, 5A, and the lanthanide rare earths. Mixtures of the aforementioned promoters can also be employed.

Any paraffinic hydrocarbon or mixture of paraffinic hydrocarbons can be employed in the process of this invention provided that an olefin, preferably, a mono-olefin, is produced. The term "paraffinic hydrocarbon", as used herein, refers to a saturated hydrocarbon. Generally, the paraffinic hydrocarbon contains at least 2 carbon atoms. Preferably, the paraffinic hydrocarbon contains from 2 to about 25 carbon atoms, preferably, from 2 to about 15 carbon atoms, and even more preferably, from 2 to about carbon atoms. The paraffinic hydrocarbon can have a linear, branched, or cyclic structure, and can be a liquid or gas at ambient temperature and pressure. The paraffinic hydrocarbon can be supplied as an essentially pure paraffinic compound or as a paraffin-containing mixture of hydrocarbons. Paraffinic hydrocarbon feeds which are suitably employed in the process of this invention include, but are not limited to, ethane, propane, butane, pentane, hexane, heptane, octane, isomers and higher homologues thereof, as well as complex higher boiling mixtures of paraffin-containing hydrocarbons, such as naphtha, gas oil, vacuum gas oil, and natural gas condensates. Additional feed components may include methane, nitrogen, carbon monoxide, carbon dioxide, and steam, if so desired. Minor amounts of unsaturated hydrocarbons may also be present. Most preferably, the paraffinic hydrocarbon is selected from ethane, propane, mixtures of ethane and propane, naphtha, gas oil, vacuum gas oil, natural gas condensates, and mixtures of the aforementioned hydrocarbons.

In the process of this invention, the paraffinic hydrocarbon is contacted with an oxygen-containing gas. Preferably, the gas is molecular oxygen or molecular oxygen diluted with an unreactive gas, such as nitrogen, helium, or argon, or diluted with a substantially unreactive gas, such as carbon monoxide or steam. Any molar ratio of paraffinic hydrocarbon to oxygen is suitable, provided the desired olefin is produced in the process of this invention. Preferably, the process is conducted fuel-rich and above the upper flammability limit. A fuel-rich feed reduces the selectivities to deep oxidation products, such as carbon monoxide and carbon dioxide, and beneficially increases the selectivity to olefins. Above the upper flammability limit, homogeneous (gas phase) combustion of the feed is not self-sustaining; therefore, the feed is safer to handle. One skilled in the art would know how to determine the upper flammability limit for different feedstream mixtures comprising the paraffinic hydrocarbon, oxygen, and optionally, hydrogen and diluent.

Generally, the molar ratio of paraffinic hydrocarbon to oxygen varies depending upon the specific paraffin feed and autothermal process conditions employed. Typically, the molar ratio of paraffinic hydrocarbon to oxygen ranges from about 3 to about 77 times the stoichiometric ratio of hydrocarbon to oxygen for complete combustion to carbon dioxide and water. Preferably, the molar ratio of paraffinic hydrocarbon to oxygen ranges from about 3 to about 13, more preferably, from about 4 to about 11, and most preferably, from about 5 to about 9 times the stoichiometric ratio of hydrocarbon to oxygen for complete combustion to carbon dioxide and water. These general limits are usually achieved by employing a molar ratio of paraffinic hydrocarbon to oxygen greater than about 0.1:1, preferably, greater than about 0.2:1, and by using a molar ratio of paraffinic hydrocarbon to oxygen usually less than about 3.0:1, preferably, less than about 2.7:1. For preferred paraffins, the following ratios are more specific. For ethane, the ethane to oxygen molar ratio is typically greater than about 1.5:1, and preferably, greater than about 1.8:1. The ethane to oxygen molar ratio is typically less than about 3.0:1, preferably, less than about 2.7:1. For propane, the propane to oxygen molar ratio is typically greater than about 0.9:1, preferably, greater than about 1.1:1. The propane to oxygen molar ratio is typically less than about 2.2:1, preferably, less than about 2.0:1. For naphtha, the naphtha to oxygen molar ratio is typically greater than about 0.3:1, preferably, greater than about 0.5:1. The naphtha to oxygen molar ratio is typically less than about 1.0:1, preferably, less than about 0.9:1. One skilled in the art can adjust the aforementioned hydrocarbon/oxygen molar ratio to higher or lower values as may be dictated by the specific feed and autothermal process conditions. For example, if the feedstream is preheated to a temperature greater than about 200° C., the ratio of the paraffinic hydrocarbon to oxygen can be shifted towards higher values, up to about 4.0:1.

Optionally, hydrogen may be co-fed with the paraffinic hydrocarbon and oxygen to the catalyst. The presence of hydrogen in the feedstream beneficially improves the conversion of hydrocarbon and the selectivity to olefins, while reducing the formation of deep oxidation products, such as, carbon monoxide and carbon dioxide. The molar ratio of hydrogen to oxygen can vary over any operable range, provided that the desired olefin product is produced. Typically, the molar ratio of hydrogen to oxygen is greater than about 0.5:1, preferably, greater than about 0.7:1, and more preferably, greater than about 1.5:1. Typically, the molar ratio of hydrogen to oxygen is less than about 3.2:1, preferably, less than about 3.0:1, and more preferably, less than about 2.7:1. The hydrogen to oxygen molar ratio may also be adjusted to higher or lower values to fit the specific feed and autothermal process conditions. For example, if the feedstream is preheated to a temperature greater than about 200° C., the hydrogen to oxygen molar ratio may be shifted to higher values, up to about 4.0:1.

Optionally, the feed may contain a diluent, which can be any gas or vaporizable liquid which essentially does not interfere with the oxidation process of the invention. The diluent functions as a carrier of the reactants and products and facilitates the transfer of heat generated by the process. The diluent also helps to minimize undesirable secondary reactions and helps to expand the non-flammable regime for mixtures of the paraffinic hydrocarbon and oxygen, and optionally hydrogen. Suitable diluents include nitrogen, argon, helium, carbon dioxide, carbon monoxide, methane, and steam. The concentration of diluent in the feed can vary over a wide range. If a diluent is used, the concentration of diluent is typically greater than about 0.1 mole percent of the total reactant feed including paraffinic hydrocarbon, oxygen, diluent, and optional hydrogen. Preferably, the amount of diluent is greater than about 1 mole percent of the total reactant feed. Typically, the amount of diluent is less than about 70 mole percent, and preferably, less than about 40 mole percent, of the total reactant feed.

The catalyst which is employed in the process of this invention beneficially comprises a Group 8B metal, and optionally, at least one promoter supported on a catalyst support, preferably, a monolith support. The Group 8B metals include iron, cobalt, nickel, and the platinum group elements, namely, ruthenium, rhodium, palladium, osmium, iridium, and platinum. Mixtures of the aforementioned Group 8B metals may also be used. Preferably, the Group 8B metal is a platinum group metal. Preferably, the platinum group metal is platinum.

The catalyst optionally comprises at least one promoter, which is suitably defined as any element or elemental ion which is capable of enhancing the performance of the catalyst, as measured, for example, by an increase in the paraffin conversion, an increase in the selectivity to olefin, a decrease in the selectivities to deep oxidation products, such as carbon monoxide and carbon dioxide, and/or an increase in catalyst stability and lifetime. Typically, the term "promoter" does not include the platinum group metals. Broadly, the promoter can be selected from Groups 1A, 2A, 3B, 4B, 5B, 6B, 1B, 3A, 4A, 5A, and the lanthanide rare earths and actinide elements of the Periodic Table, as previously referenced by S. R. Radel and M. H. Navidi, ibid. Preferably, the promoter is selected from Groups 1B, 6B, 3A, 4A, 5A, and the lanthanide elements. Mixtures of the aforementioned promoters can also be employed. More preferably, the promoter is selected from copper, tin, antimony, silver, indium, and mixtures thereof. Most preferably, the promoter is copper, tin, antimony, or a mixture thereof. If a promoter is employed, then any atomic ratio of Group 8B metal to promoter in the fresh catalyst is suitable, provided that the catalyst is operable in the process of this invention. The optimal atomic ratio will vary with the specific Group 8B metal and promoter employed. Generally, the atomic ratio of Group 8B metal to promoter is greater than about 0.10 (1:10), preferably, greater than about 0.13 (1:8), and more preferably, greater than about 0.17 (1:6). Generally, the atomic ratio of the Group 8B metal to promoter is less than about 2.0 (1:0.5), preferably, less than about 0.33 (1:3), and more preferably, less than about 0.25 (1:4). Although the promoter may be used in a gram-atom amount equivalent to or greater than the Group 8B metal, the promoter nevertheless functions to enhance the catalytic effect of the catalyst. Compositions prepared with promoter alone, in the absence of the Group 8B metal, are typically (but not always) catalytically inactive in the process. In contrast, the Group 8B metal is catalytically active in the absence of promoter metal, albeit with lesser activity.

In one form, the catalyst can be supplied as a metallic gauze. In this form, the gauze acts as both catalyst and monolith support. More specifically, the gauze can comprise an essentially pure Group 8B metal or an alloy of Group 8B metals, preferably, platinum group metals, onto which optionally a promoter is deposited. Suitable gauzes of this type include pure platinum gauze and platinum-rhodium alloy gauze, optionally coated with the promoter. The method used to deposit or coat the promoter onto the gauze can be any of the methods described hereinafter. Alternatively, a gauze comprising an alloy of a Group 8B metal and the promoter can be employed. Suitable examples of this type include gauzes prepared from platinum-tin, platinum-copper, and platinum-tin-copper alloys. During regeneration, one or more of the Group 8B alloy metals and/or the same or a different promoter can be deposited.

In another embodiment, the Group 8B metal and promoter are supported on a catalytic support. The loading of the Group 8B metal on the support can be any loading which provides for an operable catalyst in the process of this invention. In general, the loading of the Group 8B metal can be as low as about 0.0001 weight percent, based on the total weight of the Group 8B metal and support. Preferably, the loading of the Group 8B metal is greater than about 0.1 weight percent, and more preferably, greater than about 0.2 weight percent, based on the total weight of the Group 8B metal and the support. Preferably, the loading of the Group 8B metal is less than about 80 weight percent, preferably, less than about 60 weight percent, and more preferably, less than about 10 weight percent, based on the total weight of the Group 8B metal and the support. Once the Group 8B metal loading is established, the desired atomic ratio of Group 8B metal to promoter determines the loading of the promoter.

The catalytic support comprises any material which provides a surface to carry the Group 8B metal, and optionally, any promoter(s) and support modifiers, as described hereinafter. Preferably, the support is thermally and mechanically stable under autothermal process conditions. The support may exhibit essentially no activity with respect to the oxidation process and may consequently be regarded as inert. Alternatively, the support may exhibit some reactivity with respect to the oxidation process; for example, different supports may increase or decrease the conversion of the paraffinic hydrocarbon and the selectivity to olefinic products.

Preferably, the support is a ceramic, such as a refractory oxide, nitride, or carbide. Non-limiting examples of suitable ceramics include alumina, silica, silica-aluminas, aluminosilicates, for example, cordierite, as well as, magnesia, magnesium aluminate spinels, magnesium silicates, zirconia, titania, boria, zirconia toughened alumina (ZTA), lithium aluminum silicates, silicon carbide, silicon nitride, and oxide-bonded silicon carbide. Mixtures of the aforementioned refractory oxides, nitrides, and carbides may also be employed, as well as, washcoats of the aforementioned materials on a support. Preferred ceramics include magnesia, alumina, silica, and amorphous and crystalline combinations of alumina and silica, including mullite. Alpha ($\alpha$) and gamma ($\gamma$) alumina are preferred forms of alumina. Preferred combinations of alumina and silica comprise from about 65 to about 100 weight percent alumina and from essentially 0 to about 35 weight percent silica. Other refractory oxides, such as boria, can be present in smaller amounts in the preferred alumina and silica mixtures. Preferred zirconias include zirconia fully stabilized with calcia (SSZ) and zirconia partially stabilized with magnesia (PSZ), available from Vesuvius Hi-Tech Ceramics, Inc. Magnesia is the most preferred support, because it produces fewer cracking products and less carbon monoxide. Moreover, the hydrocarbon conversion and olefin selectivity tend to be higher with magnesia.

The catalytic support may take a variety of shapes including that of porous or non-porous spheres, granules, pellets, irregularly shaped solid or porous particles, or any other shape which is suitable for a variety of catalytic reactors, including fixed bed, transport bed, and fluidized bed reactors. In a preferred form, the catalyst is a monolith, which means that it is a continuous structure. Examples of monoliths include honeycomb structures, foams, and fibers woven into fabrics or made into non-woven mats or thin paper-like sheets. Foams are sponge-like structures. More preferably, the support is a foam or fiber ceramic monolith. Catalysts prepared with foam or fiber supports tend to have a higher activity as compared with catalysts prepared on solid spheres or irregularly shaped particles. Additionally, fibers tend to possess higher fracture resistance as compared with foams and honeycombs. Preferred ceramic foams, available from Vesuvius Hi-Tech Ceramics, Inc., comprise alpha alumina, zirconia, and mullite with a porosity ranging from about 5 to about 100 pores per linear inch (ppi) (2 to 40 pores per linear cm (ppcm)). Foams having about 45 ppi (18 ppcm) are more preferred. The term "porosity," as used herein, refers to channel size or dimension. It is important to note that the foam supports are not substantially microporous structures. Rather, the foams are macroporous, meaning that they are low surface area supports with channels ranging in diameter from about 0.1 mm to about 5 mm. The foams are estimated to have a surface area less than about 10 $m^2/g$, and preferably, less than about 2 $m^2/g$, but greater than about 0.001 $m^2/g$.

More preferred ceramic fibers, such as those available as Nextel® brand ceramic fibers, a trademark of 3M Corporation, typically have a diameter greater than about 1 micron ($\mu$m), preferably, greater than about 5 microns ($\mu$m). The diameter is suitably less than about 20 $\mu$m, preferably, less than about 15 $\mu$m. The length of the fibers is generally greater than about 0.5 inch (1.25 cm), preferably, greater than about 1 inch (2.5 cm), and typically less than about 10 inches (25.0 cm), preferably, less than about 5 inches (12.5 cm). The surface area of the fibers is very low, being generally less than about 1 $m^2/g$, preferably, less than about 0.3 $m^2/g$, but greater than about 0.001 $m^2/g$. Preferably, the fibers are not woven like cloth, but instead are randomly intertwined as in a mat or matted rug. Most preferred are Nextel® brand 312 fibers which consist of alumina (62 weight percent), silica (24 weight percent), and boria (14 weight percent). Non-limiting examples of other suitable fibers include Nextel® brand 440 fibers which consist of gamma alumina (70 weight percent), silica (28 weight percent), and boria (2 weight percent) and Nextel® brand 610 fibers which consist of alpha alumina (99 weight percent), silica (0.2–0.3 weight percent) and iron oxide (0.4–0.7 weight percent).

The catalyst of this invention can be synthesized "off-line," that is, outside the reactor, and then regenerated "on-line," that is, in situ. For the sake of thoroughness, the "off-line" synthesis is described in detail hereinafter. In "off-line" synthesis, the deposition of the Group 8B metal and promoter onto the support can be made by any technique known to those skilled in the art, for example, impregnation, ion-exchange, deposition-precipitation, vapor deposition, sputtering, and ion implantation. In one preferred "off-line" synthesis the Group 8B metal is deposited onto the support by impregnation. Impregnation is described by Charles N. Satterfield in *Heterogeneous Catalysis in Practice*, McGraw-Hill Book Company, New York, 1980, 82–84, incorporated herein by reference. In this procedure, the support is wetted with a solution containing a soluble Group 8B metal compound, preferably, to the point of incipient wetness. The temperature of the deposition typically ranges from about ambient, taken as 23° C., to about 100° C., preferably, from about 23° C. to about 50° C. The deposition is conducted usually at ambient pressure. Non-limiting examples of suitable Group 8B metal compounds include Group 8B metal nitrates, halides, sulfates, alkoxides, carboxylates, and Group 8B metal organometallic compounds, such as halo, amino, and carbonyl complexes. Preferably, the Group 8B metal compound is a platinum group metal compound, more preferably, a platinum group metal halide, most preferably, a platinum group chloride, such as chloroplatinic acid. The solvent can be any liquid which solubilizes the Group 8B metal compound. Suitable solvents include water, aliphatic alcohols, aliphatic and aromatic hydrocarbons, and halo-substituted aliphatic and aromatic hydrocarbons. The concentration of the Group 8B metal compound in the solution generally ranges from about 0.001 molar (M) to about 10 M. After contacting the support with the solution containing the Group 8B metal compound, the support may be dried under air at a temperature ranging from about 23° C. to a temperature below the decomposition temperature of the Group 8B metal compound, typically, a temperature between about 23° C. and about 100° C.

The deposition of the promoter can be accomplished in a manner analogous to the deposition of the Group 8B metal. Accordingly, if impregnation is used, then the support is wetted with a solution containing a soluble promoter compound at a temperature between about 23° C. and about 100° C., preferably, between about 23° C. and about 50° C., at about ambient pressure. Suitable examples of soluble promoter compounds include promoter halides, nitrates, alkoxides, carboxylates, sulfates, and promoter organometallic compounds, such as amino, halo, and carbonyl complexes. Suitable solvents comprise water, aliphatic alcohols, aliphatic and aromatic hydrocarbons, and chloro-substituted aliphatic and aromatic hydrocarbons. Certain promoter compounds, such as compounds of tin, may be more readily solubilized in the presence of acid, such as hydrochloric acid. The concentration of the promoter compound in the solution generally ranges from about 0.01 M to about 10 M. Following deposition of the soluble promoter compound or mixture thereof, the impregnated support may be dried under air at a temperature between about 23° C. and a temperature below the temperature wherein vaporization or decomposition of the promoter compound occurs. Typically, the drying is conducted at a temperature between about 23° C. and about 100° C.

In one method of preparing the catalyst, the Group 8B metal is deposited onto the support first, and thereafter the promoter is deposited onto the support. In an alternative method, the promoter is deposited first, followed by the deposition of the Group 8B metal. In a preferred method of preparing the catalyst, the Group 8B metal and the promoter are deposited simultaneously onto the support from the same deposition solution.

Following one or more depositions of the Group 8B metal and optional promoter compounds onto the support, a calcination under oxygen is optional. If performed, the calcination is conducted at a temperature ranging from about 100° C. to below the temperature at which volatilization of the metals becomes significant, typically, a temperature less than about 1,110° C. Preferably, the calcination is conducted at a temperature between about 100° C. and about 500° C.

As a final step in the "off-line" preparation of the catalyst, the fully loaded support is reduced under a reducing agent, such as hydrogen, carbon monoxide, or ammonia, at a temperature between about 100° C. and about 800° C., preferably between about 125° C. and about 600° C., so as to convert the Group 8B metal substantially into its elemental metallic form. The promoter may be fully or partially reduced, or not reduced at all, depending upon the specific promoter chosen and the reduction conditions. In addition, reduction at elevated temperatures may produce alloys of the Group 8B metal and the promoter. Alloys may provide enhanced catalyst stability by retarding vaporization of the promoter during the process of this invention.

In another preferred embodiment of the "off-line" synthesis, the support is pretreated with a support modifier prior to loading the Group 8B metal and promoter(s). The support modifier can be any metal ion having a charge of +1 or greater. Preferably, the support modifier is selected from Groups 1A, 2A, 3B, 4B, 5B, 6B, 1B, 3A, 4A, 5A, (the aforementioned being equivalent to Groups 1, 2, 3, 4, 5, 6, 11, 13, 14, 15), and the lanthanide rare earths and actinide elements (specifically thorium) of the Periodic Table, as previously referenced by S. R. Radel and M. H. Navidi, ibid. More preferably, the support modifier is selected from calcium, zirconium, tin, lanthanum, potassium, lutetium, erbium, barium, holmium, cerium, antimony, and mixtures thereof. Most preferably, the support modifier is selected from lanthanum, tin, antimony, calcium, and mixtures thereof. Certain elements, such as tin, antimony, and silver, may function as both promoter and support modifier simultaneously. As noted hereinbefore, for the purposes of this invention, the support modifier is included within the broad definition of the promoter.

The procedure to modify the support comprises contacting the support with a solution containing a soluble compound of the support modifier. The contacting can involve ion-exchange or impregnation methods. Preferably, the modification procedure involves submerging the support in the solution such that essentially all of the surface area of the support is contacted with an excess of the solution. Compounds suitable for preparing the solution of support modifier include modifier nitrates, halides, particularly the chlorides, alkoxides, carboxylates, and organometallic complexes including amino, halo, alkyl, and carbonyl complexes. Suitable solvents include water, aliphatic alcohols, aromatic hydrocarbons, and halo-substituted aliphatic and aromatic hydrocarbons. Typically, the concentration of modifier compound in the solution ranges from about 0.001 M to about 10 M. Acidified solutions, for example, of hydrochloric acid and diluted solutions thereof, may be beneficially employed. The contact time generally ranges from about 1 minute to about 1 day. The contacting temperature suitably ranges from about 23° C. to about 100° C., and pressure is generally ambient. The modified support is typically calcined, as noted hereinabove, or reduced under a reducing agent, such as hydrogen, at a temperature between about 100° C. and about 900° C., preferably, between about 200° C. and about 800° C. The choice of calcination or reduction depends on the element used to pretreat the support. If the element or its oxide is readily vaporizable, the pretreated support is reduced. If the element or its oxide is not readily vaporizable, then the pretreated support can be calcined. As a guideline, the words "readily vaporizable" may be taken to mean that greater than about 1 weight percent of any metal component in the catalyst is vaporized in a period of about 24 h under calcination conditions at about 200° C. The term "readily vaporizable" may be given a narrower or broader definition, as desired.

Following the pretreatment modification, the Group 8B metal and promoter are loaded onto the support. Then, the support is reduced as described hereinbefore. Alternatively, the metal-loaded support may be calcined first, as described hereinbefore, and then reduced. Whether the modified support is calcined or not depends again upon the vaporization potential of the modifier metal(s) and promoter(s) employed. Supports modified with metals which tend to vaporize readily are typically not calcined. Supports modified with metals that form a volatile oxide are typically not calcined. Supports modified with metals or metal oxides which do not vaporize readily can be calcined.

In another preferred aspect, the Group 8B metal and optional promoter(s) are loaded onto the front edge of the support, as opposed to being uniformly loading throughout the support. Front face (or up-front) loading leads to improved selectivity to olefins in the oxidation process of this invention. If the support is not yet loaded into the reactor, front face loading can be accomplished by conventional techniques, such as, impregnation of the front face of a blank support with solutions containing the Group 8B metal and promoter(s).

In the method of interest in this invention, the catalyst is synthesized or regenerated "on-line." On-line synthesis is accomplished by co-feeding at least one volatile Group 8B metal compound and, optionally, at least one volatile promoter compound into the reactor with the reactant feedstream under ignition conditions. In this method, a blank support, defined as a fresh support absent any Group 8B metal and promoter(s), is positioned in the reactor and heated to a temperature sufficient to effect ignition. On-line regeneration is similarly accomplished, with the exception that the deactivated or partially deactivated catalyst is positioned in the reactor and heated to autothermal conditions. On-line synthesis and regeneration yield front-face loaded catalysts, which are preferred.

In the on-line synthesis or regeneration method of this invention, the Group 8B metal and/or promoter(s) can be deposited from a vapor stream of the metallic element(s). Alternatively, any chemical compound containing the Group 8B metal and/or the promoter can be employed, provided the compound has sufficient volatility. The term "sufficient volatility" means that the Group 8B metal compound and/or promoter compound can be volatilized under the preheat conditions of the reactant feedstream, typically, a temperature between about 40° C. and about 550° C. The volatile compound(s) can be introduced continuously or intermittently into the reactant feedstream, as desired.

Non-limiting examples of suitable volatile Group 8B metal compounds and volatile promoter compounds include volatile Group 8B and promoter complexes containing ligands selected from carbonyl, halides, alkyls, monoolefins, diolefins, acetylene, allyl, cyclo(hydrocarbyl)dienes, such as cyclobutadiene and cyclooctatetraene, cyclo(hydrocarbyl)dienyls, such as cyclopentadienyl, cycloheptatrienyl, as well as aryl ligands, such as benzene, and complexes containing mixed varieties of these ligands, that is, mixed variations. Also suitable are the volatile alkoxides, oxides, and phosphines. Preferably, the volatile Group 8B metal compound is a Group 8B carbonyl, phosphine, or olefin complex, or mixed variation thereof. More preferably, the volatile Group 8B metal compound is selected from (trihalophosphine)platinum group metal complexes. Most preferably, the volatile platinum group compound is tetrakis(trifluorophosphine)platinum (0). Preferably, the volatile promoter compound is selected from promoter alkyl, amine, carbonyl, halide, and aryl complexes, and mixed variations thereof. Suitable examples of the volatile promoter compound include tetraethyltin, dichloroditolylstannane, diethyldibromodipyridinetin, diethyltin dibromide, diethyltin dichloride, dimethyldiethyltin, dimethylethylpropyltin, dimethyltin dichloride, dimethyltin dibromide, phenylbenzyltin dichloride, tribenzylethyltin, tribenzyltin chloride, tributyltin acetate, triethyltin chloride, triethyltin hydroxide, triphenylallyltin, triphenylbenzyltin, triphenylmethyltin, triphenylethyltin, triphenylbutyltin, triphenyltin bromide, triphenyltin chloride, trixylyltin halides, triethylantimony, trimethylantimony, as well as triphenylantimony, copper acetylacetonate, and ethylcopper acetylacetonate. More preferably, the volatile promoter compound is selected from promoter alkyl, carbonyl, halide, and aryl complexes, and mixed variations thereof, characterized further in that the promoter metal is selected from Groups 1B, 6B, 3A, 4A, 5A, and the lanthanide elements, and more preferably selected from tin, antimony, copper, silver, and indium. The aforementioned examples are used for illustrative purposes only and are not meant to be limiting. One skilled in the art may find other species which are equally suitable.

Any amounts of volatile Group 8B metal compound and/or volatile promoter compound can be fed to the oxidation reactor, provided that the paraffin conversion and the olefin selectivity remain at the desired levels. The preferred loadings and atomic ratios of Group 8B metal to promoter are set forth hereinabove. Typically, each volatile compound comprises from about 0.1 parts per billion (ppb) to about 5 percent, preferably, from about 0.5 parts per million (ppm) to about 1,000 ppm (0.1 percent), based on the total volume of the feedstream. The volatile compounds are fed for a period of time sufficient to deposit the desired amounts of Group 8B metal and promoter on the support.

The oxidation process and the catalyst regeneration process of this invention are both conducted under autothermal conditions. Thermal energy is needed to maintain autothermal process conditions. Without preheating the feedstream, the required thermal energy is totally supplied by the reaction of the feedstream with oxygen, namely, oxidative dehydrogenation to form olefins and water, hydrogen oxidation to form water, and carbon combustion to form carbon monoxide and carbon dioxide. Under these conditions the heat generated by the combustion of a portion of the feed is sufficient to support endothermic dehydrogenation and/or thermal cracking of the paraffin to the olefin. Accordingly, the need for an external heating source to supply the energy for the process is eliminated. As a requirement for conducting an autothermal process, the catalyst should be capable of combustion beyond the normal fuel rich limit of flammability. Alternatively, a portion of the required thermal energy can be obtained by preheating the feedstream. The preheat can be conveniently supplied by condensing high pressure saturated steam or by combusting off-gas or other fuel source. Preheat at a temperature greater than about 40° C., but below the onset of reaction of the feed components can be used without loss in olefin selectivity. As a second alternative, a portion of the required thermal energy can be obtained by adding hydrogen to the feedstream. Hydrogen reacts exothermically with oxygen to form water. When hydrogen is used in the feedstream with, optionally, a high preheat, autothermal conditions can be maintained even when the catalyst does not support combustion beyond the normal fuel-rich limit of flammability.

Ignition can be effected by preheating the feed to a temperature sufficient to effect ignition when the feed is contacted with the catalyst. Alternatively, the feed can be ignited with an ignition source, such as a spark or flame. Upon ignition, the reaction-generated heat causes the temperature to take a step change jump to a new steady state level which is herein referred to as the autothermal reaction.

While running autothermally, the paraffinic hydrocarbon feed is preferably preheated to obtain a portion of the thermal energy needed to run the oxidation process. Preheat also volatilizes the Group 8B metal compound and promoter compound(s), so as to combine them with the reactant feed.

Typical preheat temperatures range from about 40° C. to about 550° C. Preferably, the preheat temperature ranges from about 40° C. to only about 250° C., so as to prevent premature decomposition of the volatile Group 8B and promoter compounds in the feed.

As a general rule, the autothermal process operates at close to the adiabatic temperature (that is, essentially without loss of heat), which is typically greater than about 750° C., and preferably, greater than about 925° C. Typically, the autothermal process operates at a temperature less than about 1,150° C., and preferably, less than about 1,050° C. Optionally, the temperature at the reactor exit can be measured, for example, by using a Pt/Pt-Rh thin wire thermocouple. With a monolith catalyst, the thermocouple can be sandwiched between the monolith and the downstream radiation shield. Measurement of temperature close to the reactor exit may be complicated by the high temperature involved and the fragility of the thermocouple. Thus, as an alternative, one skilled in the art can calculate the adiabatic temperature at the reactor exit from a knowledge of the preheat temperature and the exit stream composition. The "adiabatic temperature" is the temperature of the product stream without heat loss, that is, when all of the heat generated by the process is used to heat the reactor contents. Typically, the measured temperature is found to be within about 25° C. of the calculated adiabatic temperature.

The operating pressure is typically equal to or greater than about 1 atmosphere absolute (atm abs) (100 kPa abs). Typically, the pressure is less than about 20 atm abs (2,000 kPa abs), preferably, less than about 10 atm abs (1,000 kPa abs), and more preferably, less than about 7 atm abs (700 kPa abs).

It is desirable to maintain a high space velocity through the reaction zone, otherwise the selectivity to olefinic products may decrease due to undesirable side reactions. The specific gas hourly space velocities employed will depend upon the choice of reactor cross sectional dimension (for example, diameter), and the form and weight of the catalyst. Generally, the gas hourly space velocity (GHSV), calculated as the total flow of the hydrocarbon, oxygen, optional hydrogen, and optional diluent flows, is greater than about 50,000 ml total feed per ml catalyst per hour ($h^{-1}$) measured at standard temperature and pressure (0° C., 1 atm) (STP). Preferably, the GHSV is greater than about 80,000 $h^{-1}$, and more preferably, greater than 100,000 $h^{-1}$. Generally, the gas hourly space velocity is less than about 6,000,000 $h^{-1}$, preferably, less than about 4,000,000 $h^{-1}$, more preferably, less than 3,000,000 $h^{-1}$, measured as the total flow at standard temperature and pressure. Gas flows are typically monitored in units of liters per minute at standard temperature and pressure (slpm). The conversion of gas flow from "slpm" units to gas hourly space velocity units ($h^{-1}$) is made as follows:

$$GHSV\, h^{-1} = \frac{\text{slpm} \times 1000 \text{ cm}^3/\text{min} \times 60 \text{ min/h}}{\text{cross-sectional area of catalyst (cm}^2\text{)} \times \text{length(cm)}}$$

The residence time of the reactants in the reactor is simply calculated as the inverse of the gas hourly space velocity. At the high space velocities employed in the process of this invention, the residence time is on the order of milliseconds. Thus, for example, a gas hourly space velocity of 100,000 $h^{-1}$ measured at STP is equivalent to a residence time of 36 milliseconds at STP.

The process of this invention may be conducted in any reactor designed for use under autothermal process conditions, including fixed bed, fluidized bed, and transport reactors. In one preferred design, the catalyst is prepared on a monolith support which is sandwiched between two radiation shields inside a reactor housing. In another preferred form, a fluidized bed reactor is used with the catalyst in the form of pellets, spheres, and other particulate shapes. More preferably, the fluidized bed has an aspect ratio less than 1:1 during operation, and even more preferably, less than 1:1 in static mode, which is the unfluidized or fixed bed configuration. The aspect ratio is the ratio of the height (or depth) of the bed to its cross-sectional dimension (diameter or width). Continuous and intermittent flow of the feedstream are both suitable.

When a paraffinic hydrocarbon is contacted with oxygen under autothermal process conditions in the presence of the catalyst described hereinabove, an olefin, preferably a mono-olefin, is produced. Ethane is converted primarily to ethylene. Propane and butane are converted primarily to ethylene and propylene. Isobutane is converted primarily to isobutylene and propylene. Naphtha and other higher molecular weight paraffins are converted primarily to ethylene and propylene.

The conversion of paraffinic hydrocarbon in the process of this invention can vary depending upon the specific feed composition, catalyst, and process conditions employed. For the purposes of this invention, "conversion" is defined as the mole percentage of paraffinic hydrocarbon in the feed which is converted to products. Generally, at constant pressure and space velocity, the conversion increases with increasing temperature. Typically, at constant temperature and pressure, the conversion does not change significantly over a wide range of high space velocities employed. In this process, the conversion of paraffinic hydrocarbon is typically greater than about 45 mole percent, preferably, greater than about 50 mole percent, and more preferably, greater than about 60 mole percent.

Likewise, the selectivity to products will vary depending upon the specific feed composition, catalyst, and process conditions employed. For the purposes of this invention, "selectivity" is defined as the percentage of carbon atoms in the converted paraffin feed which reacts to form a specific product. For example, the olefin selectivity is calculated as follows:

$$\frac{\text{Moles of olefin formed} \times \text{Number of carbon atoms in olefin} \times 100}{\text{Moles of paraffin converted} \times \text{Number of carbon atoms in paraffin}}$$

Generally, the olefin selectivity increases with increasing temperature up to a maximum value and declines as the temperature continues to rise. Usually, the olefin selectivity does not change substantially over a wide range of high space velocities employed. In the process of this invention, the olefin selectivity, preferably the combined olefin selectivity to ethylene and propylene, is typically greater than about 50 carbon atom percent, preferably, greater than about 60 carbon atom percent, more preferably, greater than about 70 carbon atom percent, and even more preferably, greater than about 80 carbon atom percent. Other products formed in smaller quantities include methane, carbon monoxide, carbon dioxide, propane, butenes, butadiene, propadiene, acetylene, methylacetylene, and $C_{6+}$ hydrocarbons. Acetylene can be hydrogenated downstream to increase the overall selectivity to olefin. Carbon monoxide, carbon dioxide, and methane can be recycled, at least in part, to the reactor.

Water is also formed in the process of this invention from the reaction of hydrogen or hydrocarbon with oxygen. The presence of hydrogen in the feed minimizes the formation of carbon oxides by reacting with the oxygen to produce water and energy. Accordingly, it is advantageous to recycle the hydrogen in the product stream, obtained from the dehydrogenation of the paraffin, back to the reactor. Optimally, the hydrogen needed to meet the demands of the process essentially equals the hydrogen formed during conversion of the paraffin to olefin. Under these balanced conditions, the hydrogen forms a closed loop wherein there is essentially no demand for additional hydrogen to be added to the feed. Such conditions are more easily met when the feed is preheated and a higher hydrocarbon to oxygen molar ratio is employed.

Over time the catalyst loses activity due to the loss of catalytic components by vaporization. In the method of this invention a partially deactivated catalyst can be easily regenerated on-line during the autothermal oxidation process. A fully-deactivated catalyst can be regenerated on-line under ignition conditions. With this regeneration method, there is no need to shut down the process and remove the catalyst from the reactor. Rather, the regeneration is effected by co-feeding a volatile Group 8B metal compound and/or a volatile promoter compound with the oxidation reactant feed under autothermal or ignition operating conditions. Intermittent or continuous feeding of the volatile Group 8B metal compound and/or the volatile promoter compound are both suitable. The volatile compound(s) contact(s) the front face of the catalyst and decompose(s) at the elevated temperature of autothermal or ignition conditions into the corresponding Group 8B metal and/or promoter(s).

The invention will be further clarified by a consideration of the following examples, which are intended to be purely illustrative of the use of the invention. Other embodiments of the invention will be apparent to those skilled in the art from a consideration of this specification or practice of the invention as disclosed herein. Unless otherwise noted, all percentages are given on a mole percent basis. Selectivities are given on a carbon atom percent basis.

EXAMPLE 1

Catalyst preparation: An alumina foam monolith support (99.5 weight percent alumina; 17 mm Outside Diameter (O.D.)×10 mm length; 45 pores per linear inch) was modified with lanthanum by soaking it in an aqueous solution of lanthanum chloride (1 M). The lanthanum-modified support was calcined at 900° C., and then further modified with tin by soaking it in an aqueous solution of stannous chloride (0.372 M) to which hydrochloric acid was added to aid solubility. The tin and lanthanum modified support was dried at 100° C. and then reduced at 700° C. in flowing hydrogen (5 percent hydrogen in nitrogen). The reduced support was then loaded with a solution prepared from stock aqueous solutions of hexachloroplatinic acid (1 ml, 0.193 M) and copper nitrate (0.65 ml, 1.49 M). Platinum loading was 1.0 weight percent. Copper/platinum atomic ratio was 5:1. The loaded monolith was dried at 100° C. and then reduced at 450° C. in flowing hydrogen to yield the catalyst.

Oxidation Process: The catalyst was sandwiched between 4 inert blank alumina monoliths (2 on either side; 17 mm×10 mm) which acted as radiation shields. The five monoliths were wrapped in FiberFrax® brand alumina-silica cloth 1/16 inch (1.6 mm) thick and packed into a quartz tube (19 mm Inside Diameter (I.D.)×5 cm length). FiberFrax® is a trademark of the Unifrax Corporation. The quartz tube was then wrapped with FiberFrax® silica-alumina cloth 1/8 inch (3.2 mm) thick and packed into a stainless steel reactor 1 inch (2.5 cm) O.D. The feed to the reactor was-preheated with heating tape 10 inches (25 cm) wrapped around the stainless steel reactor upstream of the catalyst. The catalyst zone was not heated, but was insulated with high temperature insulation material to minimize heat losses. Ethane, hydrogen, and nitrogen were preheated to 200° C. and fed to the reactor. Oxygen was then introduced to the reactor which resulted in catalyst ignition. Upon ignition the temperature rose quickly within a few seconds to 1,000° C. and the reactor operated autothermally. Process conditions and results are set forth in Table 1. It was found that the ethane conversion decreased from 66.50 percent to 61.95 percent over a period of about 213 h. Over the same period the selectivity to ethylene decreased from 81.13 to 80.32 percent, while the carbon monoxide selectivity increased from 6.07 to 8.82 percent.

At 216 h on steam, a first regeneration was conducted as follows. Tetraethyltin (0.4 ml) was added through a septum into an argon line connected to the feedstream inlet just before the catalyst. The flow of argon was maintained at 0.2 slpm. The addition of the volatile tin compound was carried out "on-line" for 20 min during which time the reactor was run autothermally at 1,000° C. at the following conditions: flow, 7 slpm; nitrogen dilution, 20 percent; $C_2H_6/O_2$ molar ratio of 2; $H_2/O_2$ molar ratio of 2; 200° C. preheat. A moderately low preheat was used to prevent decomposition of the vapors of tetraethyltin before they reached the catalyst. Results after the first regeneration are set forth in Table 1.

It was found that the losses in ethane conversion and ethylene selectivity were completely recovered by the on-line addition of tetraethyltin. The tetraethyltin (partially or fully vaporized) with the argon entered the reactor just before the catalyst pack and was swept by the flow of the feed gases through the two upstream radiation shields to the hot, ignited catalyst where the organotin compound decomposed to deposit tin on the front edge of the catalyst. A sample of the effluent taken only 20 min after the tin injection showed that the ethane conversion and ethylene selectivity were recovered to the initial value at 2.8 h.

After regeneration, the process was run for an additional 291 h up to 508.5 h on stream, during which time the ethane conversion and ethylene selectivity gradually decreased, as shown in Table 1.

After 508.5 h total run time, the reactor design was modified to flow an argon stream (0.1 slpm) continuously over the surface of a reservoir of tetraethyltin at room temperature to obtain continuous regeneration. The concentration of tetraethyltin in the argon stream was expected to correspond to the vapor pressure of tetraethyltin at room temperature; however, this data was not readily available. Transdecalin has a similar boiling point and flash point as tetraethyltin. Accordingly, the vapor pressure of transdecalin was used to estimate the concentration of tetraethyltin in the argon stream. At 25° C. the vapor pressure of transdecalin is 1649 ppm. Thus, when the argon stream was mixed with the feed for the oxidation process (7.5 slpm), the tetraethyltin concentration was estimated to be approximately 22 ppm. The results of the continuous addition are set forth in Table 1 (second regeneration). It can be seen that the ethane conversion was 1 percent higher with continuous addition of about 22 ppm tetraethyltin. Higher concentrations of tetraethyltin should result in further improvements.

After 577.8 h total run time, the continuous addition of tetraethyltin was turned off and a slug of tetraethyltin (0.5 ml) was added to the argon stream through a septum. As with the first regeneration, the conversion and selectivity improved significantly and the catalyst was fully regenerated, as shown in Table 1 (third regeneration).

TABLE 1

Before and After Regeneration[a,b]

| Time (h) | $C_2H_6/O_2$ | $H_2/O_2$ | T pre-heat (° C.) | % $C_2H_6$ Conv | % $C_2H_4$ Sel | % $CH_4$ Sel | % CO Sel | % $CO_2$ Sel |
|---|---|---|---|---|---|---|---|---|
| 2.8 | 2.3 | 2.3 | 250 | 66.50 | 81.13 | 5.96 | 6.07 | 2.24 |
| 28.1 | 2.2 | 2.2 | 300 | 66.65 | 80.92 | 5.54 | 7.88 | 1.62 |
| 78 | 2.2 | 2.2 | 300 | 64.03 | 80.53 | 5.44 | 8.47 | 1.44 |
| 126 | 2.2 | 2.2 | 300 | 63.47 | 80.28 | 5.48 | 8.84 | 1.37 |
| 216 | 2.2 | 2.2 | 300 | 61.95 | 80.32 | 5.46 | 8.82 | 1.31 |
| After first regeneration (on-line slug): | | | | | | | | |
| 216.8 | 2.2 | 2.2 | 288 | 67.00 | 81.16 | 6.37 | 6.44 | 0.85 |
| 218 | 2.2 | 2.2 | 300 | 66.32 | 81.25 | 6.09 | 7.44 | 0.81 |
| Continued run: | | | | | | | | |
| 291.0 | 2.2 | 2.2 | 300 | 63.78 | 80.32 | 5.81 | 8.98 | 0.89 |
| 508.5 | 2.2 | 2.2 | 300 | 62.52 | 80.09 | 5.53 | 9.42 | 0.94 |
| Second regeneration (continuous on-line): | | | | | | | | |
| 516.2 | 2.2 | 2.2 | 300 | 63.42 | 80.37 | 5.69 | 9.05 | 0.81 |
| 542.8 | 2.2 | 2.2 | 300 | 63.51 | 80.36 | 5.80 | 9.09 | 0.81 |
| 577.8 | 2.2 | 2.2 | 300 | 63.82 | 80.37 | 5.82 | 8.94 | 0.78 |
| After third regeneration (on-line slug): | | | | | | | | |
| 585.7 | 2.2 | 2.2 | 300 | 69.38 | 81.03 | 6.71 | 6.08 | 0.70 |

[a]$C_2H_6/O_2$ and $H_2/O_2$ given as molar ratios; Inlet Pressure: 1.35 bar abs; Flow rate: 7.5 slpm; GHSV: 178, 839 $h^{-1}$; Nitrogen dilution: 10 percent; Calculated adiabatic temperature: 950–1,050° C.
[b]% Conv = mole percentage converted ethane; % Sel = percentage selectivity to product on a carbon atom basis

What is claimed is:

1. An improved process of preparing an olefin wherein a paraffinic hydrocarbon having from 2 to about 25 carbons atoms or mixture thereof is contacted with oxygen in the presence of a catalyst comprising at least one Group 8B metal, and optionally, at least one promoter metal or metal ion on a support, the contacting being conducted under autothermal process conditions sufficient to prepare the olefin in a reactor, wherein the improvement comprises simultaneously co-feeding into the reactor with the paraffinic hydrocarbon and oxygen, a volatile Group 8B metal compound, and optionally, a volatile promoter, compound continuously or intermittently so as to regenerate the catalyst on-line.

2. The process of claim 1 wherein the paraffinic hydrocarbon is selected from the group consisting of ethane, propane, and mixtures thereof.

3. The process of claim 1 wherein the paraffinic hydrocarbon is selected from the group consisting of naphtha, natural gas condensates, gas oils, vacuum gas oils, and mixtures thereof.

4. The process of claim 1 wherein the molar ratio of paraffinic hydrocarbon to oxygen ranges from about 3 to about 77 times the stoichiometric ratio of hydrocarbon to oxygen for complete combustion to carbon dioxide and water.

5. The process of claim 1 wherein the molar ratio of paraffinic hydrocarbon to oxygen is about 0.1:1 to about 4.0:1.

6. The process of claim 1 wherein the process is operated in the presence of a diluent.

7. The process of claim 6 wherein the diluent is used in an amount of about 0.1 mole percent to about 70 mole percent, based on the total reactant feed.

8. The process of claim 1 wherein, hydrogen is added to the paraffinic hydrocarbon.

9. The process of claim 1 wherein the Group 8B metal is a platinum group metal.

10. The process of claim 9 wherein the platinum group metal is platinum.

11. The process of claim 1 wherein the support is a ceramic monolith support selected from the group consisting of silica, alumina, silica-aluminas, aluminosilicates, zirconia, magnesia, magnesium aluminate spinels, magnesium silicates, titania, boria, zirconia toughened alumina, lithium aluminum silicates, silicon carbide, silicon nitride, and oxide-bonded silicon carbide.

12. The process of claim 11 wherein the ceramic monolith support comprises from about 60 to about 100 weight percent alumina.

13. The process of claim 1 wherein the promoter metal or metal ion is selected from the group consisting of Groups 1A, 2A, 3B, 4B, 5B, 6B, 1B, 3A, 4A, 5A, the lanthanide and actinide elements of the Periodic Table, and mixtures thereof.

14. The process of claim 1 wherein the atomic ratio of Group 8B metal to promoter metal or metal ion in the fresh catalyst ranges from of about 1:10 to about 1:0.5.

15. The process of claim 1 wherein the process is conducted at a temperature of about 750° C. to about 1,150° C.

16. The process of claim 1 wherein the process is conducted at a pressure of about 1 atm abs to about 20 atm abs.

17. The process of claim 1 wherein the process is conducted at a gas hourly space velocity of about 80,000 $h^{-1}$ to about 6,000,000 $h^{-1}$.

18. The process of claim 1 wherein the conversion of paraffinic hydrocarbon is about 50 mole percent or higher.

19. The process of claim 1 wherein the olefin selectivity is about 60 carbon atom percent or higher.

20. The process of claim 1 wherein the volatile Group 8B metal compound is a compound or complex containing carbonyl, alkyl, halo, mono-olefin, diolefin, acetylene, allyl, cyclo(hydrocarbyl)diene, cyclo(hydrocarbyl)dienyl, aryl, alkoxide, oxide, phosphine, or mixtures thereof.

21. The process of claim 1 wherein the volatile promoter compound is a compound or complex containing carbonyl, alkyl, halo, mono-olefin, diolefin, acetylene, allyl, cyclo(hydrocarbyl)diene, cyclo(hydrocarbyl)dienyl, aryl, alkoxide, oxide, phosphine, or mixtures thereof.

22. The process of claim 1 wherein the support is pretreated with an element selected from the group consisting of Groups 1A, 2A, 3B, 4B, 5B, 6B, 1B, 3A, 4A, 5A, the lanthanide and actinide elements, and mixtures thereof.

* * * * *